United States Patent
Resheski-Wedepohl et al.

(10) Patent No.: US 6,656,913 B1
(45) Date of Patent: Dec. 2, 2003

(54) INHIBITION OF EXOPROTEIN PRODUCTION FROM GRAM POSITIVE BACTERIA

(75) Inventors: Kim L. Resheski-Wedepohl, Reedsville, WI (US); Rae Ellen Syverson, Fond du Lac, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 184 days.

(21) Appl. No.: 09/723,589

(22) Filed: Nov. 28, 2000

(51) Int. Cl.⁷ .............. A61K 31/047; A01N 25/34; C12N 1/20; A61F 13/00

(52) U.S. Cl. .............. 514/25; 424/402; 424/404; 424/411; 424/430; 424/431; 435/252.1

(58) Field of Search ............... 424/402, 404, 424/411, 430, 431; 435/252.1; 514/25

(56) References Cited

U.S. PATENT DOCUMENTS

| | | | |
|---|---|---|---|
| 4,405,323 A | 9/1983 | Auerbach | 604/285 |
| 4,413,032 A | 11/1983 | Hartmann et al. | 428/288 |
| 4,413,986 A | 11/1983 | Jacobs | 604/14 |
| 4,424,054 A | 1/1984 | Conn et al. | 604/11 |
| 4,431,427 A | 2/1984 | Lefren et al. | 604/285 |
| 4,585,792 A | 4/1986 | Jacob et al. | 514/474 |
| 4,722,936 A | 2/1988 | Jacob | 514/474 |
| 4,722,937 A | 2/1988 | Jacob et al. | 514/474 |
| 4,769,021 A | 9/1988 | Kass | 604/367 |
| 4,952,211 A | 8/1990 | Snider | 604/285 |
| 5,000,749 A | 3/1991 | LeVeen et al. | 604/904 |
| 5,070,889 A | 12/1991 | Leveen et al. | 128/830 |
| 5,071,648 A | 12/1991 | Rosenblatt | 424/78.06 |
| 5,156,164 A | 10/1992 | LeVeen et al. | 128/832 |
| 5,221,693 A | 6/1993 | Shetty | 514/635 |
| 5,270,032 A | 12/1993 | Pollock et al. | |
| 5,342,331 A | 8/1994 | Silber et al. | 604/330 |
| 5,389,374 A | 2/1995 | Brown-Skrobot | 424/431 |
| 5,476,455 A | 12/1995 | Silber | 604/330 |
| 5,498,252 A | 3/1996 | Silber | 604/330 |
| 5,527,892 A | 6/1996 | Borsotti et al. | 536/18.6 |
| 5,540,979 A | 7/1996 | Yahiaoui et al. | 428/212 |
| 5,547,985 A | 8/1996 | Brown-Skrobot et al. | 514/546 |
| 5,601,814 A | 2/1997 | Barton et al. | 424/85.2 |
| 5,612,045 A | 3/1997 | Syverson | 424/402 |
| 5,618,554 A | 4/1997 | Syverson | 424/431 |
| 5,641,503 A | 6/1997 | Brown-Skrobot | 424/431 |
| 5,679,369 A | 10/1997 | Brown-Skrobot | 424/431 |
| 5,685,872 A | 11/1997 | Syverson | 604/360 |
| 5,705,182 A | 1/1998 | Brown-Skrobot | 424/431 |
| 5,719,113 A | 2/1998 | Fendler et al. | |
| 5,753,252 A | 5/1998 | Brown-Skrobot | 424/431 |
| 5,770,543 A | 6/1998 | Garst et al. | 504/116 |
| 5,814,567 A | 9/1998 | Yahiaoui et al. | 442/118 |
| 5,817,047 A | 10/1998 | Osborn, III et al. | 604/14 |
| 5,932,495 A | 8/1999 | Boney et al. | 442/121 |
| 5,945,175 A | 8/1999 | Yahiaoui et al. | 427/534 |
| 6,017,832 A | 1/2000 | Yahiaoui et al. | 442/118 |
| 6,028,016 A | 2/2000 | Yahiaoui et al. | 442/118 |
| 6,039,716 A | 3/2000 | Jessup et al. | 604/385.1 |
| 6,060,636 A | 5/2000 | Yahiaoui et al. | 604/367 |
| 6,063,335 A | 5/2000 | Pirolo et al. | |
| 6,107,268 A | 8/2000 | Yahiaoui et al. | 510/438 |
| 6,149,934 A | 11/2000 | Krzysik et al. | |
| 6,159,924 A | 12/2000 | Weller et al. | |
| 6,177,367 B1 | 1/2001 | Mathis | |
| 6,231,557 B1 | 5/2001 | Krautkramer et al. | |
| 6,296,936 B1 | 10/2001 | Yahiaoui et al. | |
| 6,350,711 B1 | 2/2002 | Potts et al. | |
| 6,410,039 B1 | 6/2002 | Walker | |

FOREIGN PATENT DOCUMENTS

| | | |
|---|---|---|
| EP | 0 009 977 A1 | 4/1980 |
| EP | 0 053 221 A2 | 6/1982 |
| EP | 0 110 793 B1 | 6/1984 |
| EP | 0 391 741 A2 | 10/1990 |
| EP | 0 395 099 A2 | 10/1990 |
| EP | 0 483 812 B1 | 5/1992 |
| EP | 0 483 835 A1 | 5/1992 |
| EP | 0 683 260 A2 | 11/1995 |
| GB | 1068667 | 5/1967 |
| WO | WO 87/03208 | 6/1987 |
| WO | WO 94/22501 | 10/1994 |
| WO | WO 98/09662 | 3/1998 |
| WO | WO 98/41179 | 9/1998 |
| WO | WO 99/12505 | 3/1999 |
| WO | WO 99/61079 | 12/1999 |

OTHER PUBLICATIONS

Bohach, G. A. et al. CRC Crit. Rev. Microbiology. 1990, 17(4): 251–272.*
Projan, S.J. et al .1994. J. Bacteriology, 176:4204–4209.*
Matsumura et al., "Surface Activities, Biodegradability and Antimicrobial Properties of n–Alkyl Glucosides, Mannosides and Galactosides", *Journal of the American Oil Chemists' Society*, 67, pp. 996–1000 (Dec., 1990).

* cited by examiner

*Primary Examiner*—Jon P. Weber
*Assistant Examiner*—Kailash C. Srivastava
(74) *Attorney, Agent, or Firm*—Senniger, Powers, Leavitt & Roedel

(57) ABSTRACT

A method of inhibiting the production of exoproteins from Gram positive bacteria, such as harmful proteins produced by Staphylococcus species, is described. The method is particularly useful for inhibiting the production of TSST-1, alpha-toxin and/or enterotoxins A, B and C from *S. aureus* bacteria. The method may be based on exposing Gram positive bacteria to alkyl polyglycoside incorporated into an absorbent product. Alternatively, the methods can include causing Gram positive bacteria to come into contact with the alkyl polyglycoside in other forms, e.g., when formulated with a pharmaceutically acceptable carrier or incorporated in or on a non-absorbent substrate. Typically, the alkyl polyglycoside has an HLB of at least about 10 and an alkyl group with an average of 8 to 14 carbon atoms.

11 Claims, No Drawings

INHIBITION OF EXOPROTEIN PRODUCTION FROM GRAM POSITIVE BACTERIA

BACKGROUND

Disposable absorbent devices for the absorption of human exudates are widely used. These disposable absorbent devices typically have a mass of absorbent formed into a desired shape, which is typically dictated by the intended consumer use. In the area of a catamenial tampon, the disposable absorbent article is intended to be inserted in a body cavity for absorption of the body fluids generally discharged during a woman's menstrual period.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal exudate. The bacterial flora of the vagina is comprised of both aerobic and anaerobic bacteria. The more commonly isolated bacteria are Lactobacillus species, corynebacteria, *Gardnerella vaginalis*, Staphylococcus species, Peptococcus species, aerobic and anaerobic Streptococcal species and Bacteroides species. Other microorganisms that have been isolated from the vagina on occasion include yeasts (e.g., *Candida albicans*), protozoas (e.g., *Trichomonas vaginalis*), mycoplasmas (e.g., *Mycoplasma hominis*), chlamydias (e.g., *Chlamydia trachomatis*) and viruses (e.g., *Herpes simplex*). These latter organisms are generally associated with vaginitis or venereal disease, although they may be present in low numbers without causing symptoms.

Physiological, social and idiosyncratic factors affect the quantity and species of bacteria present in the vagina. Physiological factors include age, day of the menstrual cycle and pregnancy. For example, vaginal flora present in the vagina throughout the menstrual cycle can include Lactobacillus species, corynebacterium and mycoplasma. Social and idiosyncratic factors include method of birth control, sexual practices, systemic disease (e.g., diabetes) and medication.

Bacterial proteins and metabolic products produced in the vagina can affect other microorganisms and the human host. For example, the vagina between menstrual periods is mildly acidic having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and makes the vagina inhospitable to some species of bacteria such as *Staphylococcus aureus* (*S. aureus*). The low pH is a consequence of the growth of lactobacilli and their production of acidic products. Microorganisms in the vagina can also produce antimicrobial compounds such as hydrogen peroxide and bactericides directed at other bacterial species. One example is the lactocins, products of lactobacilli directed against other species of lactobacilli.

Some microbial products may affect the human host. For example, *S. aureus* can produce and, excrete into its environment a variety of exoproteins including enterotoxins, Toxic Shock Syndrome Toxin-1 ("TSST-1") and enzymes such as protease and lipase. *S. aureus* is found in the vagina of approximately 16% of healthy women of menstrual age. Approximately 25% of the *S. aureus* isolated from the vagina are capable of producing TSST-1.

Menstrually occurring Toxic Shock Syndrome (TSS), a severe and sometimes fatal multi-system disease, is associated with colonization by *S. aureus*. This disease has been associated with the use of tampons during menstruation. The disease is caused by TSST-1 and other staphylococcal enterotoxins.

Symptoms of TSS generally include fever, diarrhea, vomiting and a rapid drop in blood pressure. A characteristic rash is usually present. Systemic vital organ failure occurs in approximately 6% of those who contact the disease. *S. aureus* does not initiate TSS as a result of the invasion of the microorganism into the vaginal cavity. Instead as *S. aureus* grows and multiplies, it can produce TSST-1. Only after entering the bloodstream does TSST-1 act systemically and produce the symptoms attributed to TSS.

There have been numerous attempts to reduce or eliminate pathogenic microorganisms and menstrually occurring TSS by incorporating into a tampon pledget one or more biostatic, biocidal, and/or detoxifying compounds. For example, L-ascorbic acid has been applied to a menstrual tampon to detoxify toxin found in the vagina of the human female during menstruation.

Others have incorporated monoesters and diesters of polyhydric aliphatic alcohols and a fatty acid containing from 8 to 18 carbon atoms. For example, glycerol monolaurate (GML) has been used to retard the production of *S. aureus* enterotoxins and TSST-1. However, as noted above, esterase is abundantly present in the vaginal epithelium and menstrual fluid. This esterase, in combination with esterase and lipase produced by bacteria can enzymatically degrade the esters into non-effective compounds. Thus, one or more ester compounds may have to be added to the absorbent article, such as a tampon pledget, in such high concentrations that the normal flora present in the vaginal area is disrupted. When the natural condition is altered, overgrowth by pathogens may take place resulting in a condition known as vaginitis. The use of other non-ionic surfactants, such as alkyl ethers, alkyl amine and alkyl amides, has been reported as a means of avoiding the problem of degradation by esterase (see, e.g., U.S. Pat. Nos. 5,685,872; 5,618,554 and 5,612,045).

A need continues to exist for agents that will effectively inhibit the production of exoproteins, such as TSST-1, from Gram positive bacteria. It would be advantageous if such agents have other desirable surface active properties, such the ability to affect wetting of coated surfaces and, in particular, the wetting of absorbent materials. The material may either be in the form of an absorbent product that has the agent incorporated therein or in other forms, e.g., coated on a non-absorbent substrate or formulated with a pharmaceutically acceptable carrier. Such agents desirably would be substantially unaffected by the enzymes lipase and esterase and, in addition, should not substantially alter the natural flora found in the vaginal area.

SUMMARY

It has been found that alkyl polyglycoside compounds are particularly effective for inhibiting the production of exoprotein(s) of Gram positive bacterium. Exposure to effective amounts of the alkyl polyglycoside can inhibit the production of potentially harmful toxins, such as those produced by Staphylococcus and/or Streptococcal species. For example, the alkyl polyglycoside can be utilized to inhibit the production of TSST-1, alpha toxin and/or enterotoxins. A, B and C from *S. aureus* bacterium. The alkyl polyglycoside typically has a hydrophilic/lipophilic balance ("HLB") of at least about 10 and/or an average number of carbon atoms in the alkyl chain of about 8 to about 14. The alkyl polyglycoside may be used alone or in combination with one or more other surfactants (e.g., myreth-3-myristate, glycerol monolaurate and/or laureth-4) and/or other additives (e.g., reducing agent(s) such as ascorbic acid, sodium bisufite, vitamin E). Such reducing agents can act as oxygen inhibiting agents and may enhance the combinations ability to reduce toxin production.

The present alkyl polyglycoside compositions are materials which, when exposed to *S. aureus* or other Gram positive bacteria in disposable absorbent articles, can reduce the production of exoproteins, such as TSST-1. It is also believed that the compounds in the present compositions are effective in combating the production of other types of bacterial toxins, in particular, alpha toxin and Staphylcoccal enterotoxins A, B, and C. The alkyl polyglycosides described herein are effective at inhibiting the production with respect to these aforementioned exoproteins when the compound is placed on an absorbent material or caused to come into contact with Gram positive bacterium in other forms, e.g., when formulated with a pharmaceutically acceptable carrier or incorporated in or on a non-absorbent substrate. The alkyl polyglycoside may be used in combination with one or more other additives, e.g., in combination with surfactants such as myreth-3-myristate, glycerol monolaurate and/or laureth-4.

The present alkyl polyglycosides are particularly useful for inhibiting the production of bacterial exotoxins when incorporated into or on disposable absorbent articles. The absorbent products are exemplified herein as described detail in connection with a catamenial tampon but would be understood by persons skilled in the art to be applicable to other disposable absorbent articles, such as: sanitary napkins, panty liners, adult incontinent undergarments, diapers, medical bandages and tampons such as those intended for medical, dental, surgical, and/or nasal use where inhibition of exoproteins from Gram positive bacteria would be beneficial. In addition, as mentioned above, inhibition of the production of bacterial exotoxins may be accomplished through incorporation of alkyl polyglycoside in liquid compositions (e.g., vaginal cleansing compositions) or non-absorbent substrates. Examples of suitable non-absorbent substrates which have alkyl polyglycoside incorporated in or on at least a portion of the device include non-absorbent incontinent devices, barrier birth control devices and contraceptive sponges. One example of a non-absorbent incontinent device is a female barrier incontinent device, such as an incontinent pledget formed from a resilient material like rubber. As used herein, the term "pledget" means a compress used to apply pressure or press upon a body part.

When employed as part of a catamenial tampon or sanitary napkin or otherwise introduced into a region affecting the vagina, the alkyl polyglycoside desirably is utilized in a manner and amount so as to minimize its effect on the natural vaginal flora. The present alkyl polyglycoside compositions are generally capable of substantially inhibiting the production of exoproteins from Gram positive bacteria, e.g., by reducing the amount of exoproteins produced by at least about 75% and desirably by at least about 90%.

The alkyl polyglycoside compositions of the present invention may additionally include adjunct components conventionally found in pharmaceutical compositions in their art-established fashion and at their art-established levels. For example, the compositions may contain additional compatible pharmaceutical materials for combination therapy, such as supplementary antimicrobials, anti-parasitic agents, antipruritics, local anesthetics, or anti-inflammatory agents.

As used herein the term "nonwoven fabric or web" means a web having a structure of individual fibers or threads which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, and bonded carded web processes. The basis weight of nonwoven fabrics is usually expressed in ounces of material per square yard ("osy") or grams per square meter ("gsm") and the fiber diameters useful are usually expressed in microns. Basis weights can be converted from osy to gsm simply by multiplying the value in osy by 33.91.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. Nos. 4,340,563; 3,692,618; 3,802,817; 3,338,992; 3,341,394; 3,502,763; 3,502,538; and 3,542,615. Spunbond fibers are quenched and generally not tacky when deposited onto a collecting surface. Spunbond fibers are generally continuous and have average diameters frequently larger than 7 microns, typically between about 10 and 20 microns.

As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly disbursed meltblown fibers. Such a process is disclosed, for example, in U.S. Pat. No. 3,849,241. Meltblown fibers are microfibers which may be continuous or discontinuous and are generally smaller than 10 microns in average diameter.

As used herein "bonded carded webs" or "BCW" refers to nonwoven webs formed by carding processes as are known to those skilled in the art and further described, for example, in U.S. Pat. No. 4,488,928 which is incorporated herein by reference. Briefly, carding processes involve starting with a blend of, for example, staple fibers with bonding fibers or other bonding components in a bulky ball that is combed or otherwise treated to provide a generally uniform basis weight. This web is heated or otherwise treated to activate the adhesive component resulting in an integrated, usually lofty nonwoven material.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer shall include all possible geometrical configurations of the material. These configurations include, but are not limited to isotactic, syndiotactic and random symmetries.

As used herein, the term "hydrophilic" means that the polymeric material has a surface free energy such that the polymeric material is wettable by an aqueous medium, i.e. a liquid medium of which water is a major component. The term "hydrophobic" includes those materials that are not hydrophilic as defined. The phrase "naturally hydrophobic" refers to those materials that are hydrophobic in their chemical composition state without additives or treatments affecting the hydrophobicity. It will be recognized that hydrophobic materials may be treated internally or externally with surfactants and the like to render them hydrophilic.

As used herein, the phrase "complex body fluid" is intended to describe a fluid generally characterized as being a viscoelastic mixture including specific components having generally inhomogeneous physical and/or chemical properties. It is the inhomogeneous properties of the specific components that often challenge the efficacy of absorbent articles in the handling of complex fluids, such as, for example, blood, menses, loose passages, nasal discharges and the like. In contrast with complex fluids, simple fluids, such as, for example, urine, physiological saline, water and the like, are generally characterized as being Newtonian and including one or more components having generally homogeneous physical and/or chemical properties. As a result of having homogeneous properties, the one or more components of simple fluids behave substantially similarly during absorption or adsorption.

The term "surface" and its plural generally refer herein to the outer or the topmost boundary of an object.

As used herein, the phrase "absorbent article" refers to devices which absorb and contain body fluids, and more specifically, refers to devices which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to: health care related products including bandages and tampons such as those intended for medical, dental, surgical and/or nasal use; personal care absorbent products such as feminine hygiene products (e.g., sanitary napkins, panty liners and catamenial tampons), diapers, training pants, incontinent products and the like, wherein the inhibition of the production of exoproteins from Gram positive bacteria would be beneficial.

DETAILED DESCRIPTION

Disposable absorbent articles which are suitable for use in the present method generally are particularly adapted to receive simple and/or complex body fluids. For purposes of discussion, the absorbent article specifically discussed herein is a catamenial tampon. However, it would be readily understood by persons skilled in the art that the present method may also employ other disposable absorbent articles wherein inhibition of exoproteins from Gram positive bacteria would be beneficial.

Specifically, catamenial tampons suitable for use in the present invention include an absorbent. The absorbent can be formed from fibers which are assembled into an absorbent sheet or ribbon. Alternatively, the absorbent can be formed from absorbent fibers which are assembled and compressed into a generally elongated and/or cylindrical configuration. The absorbent is desirably formed from cellulosic fibers, such as cotton and rayon. For example, the absorbent can be 100% cotton, 100% rayon, a blend of cotton and rayon fibers, or other materials known to be suitable for tampons.

The present alkyl polyglycoside compositions, when exposed to $S.$ $aureus$ or other Gram positive bacteria in disposable absorbent articles, can reduce the production of harmful exoproteins. In particular, exposure to the alkyl polyglycoside(s) can inhibit the production of harmful proteins produced by Staphylococcus and/or Streptococcal species.

The alkyl polyglycoside can generally be represented by the formula:

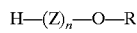

where "Z" is a saccharide residue having 5 or 6 carbon atoms, "n" is a number having a value between 1 and about 6, and "R" represents an alkyl group, typically having 8 to 18 carbon atoms. The "n" represents the average number of saccharide residues in a particular sample of alkyl polyglycoside. Although, as indicated above, the present alkyl polyglycosides can include an oligosaccharide, e.g., where n equals about 4–6, alkyl polyglycosides with a smaller average number of saccharide residues are commonly preferred. Typically, the present alkyl polyglycosides have an "n" which is no more than about 4 and, desirably no more than about 2. As defined herein, the term "alkyl polyglycoside" also encompasses alkyl monosaccharides, i.e., where "n" equals 1.

It will be understood that as referred to herein, an "alkyl polyglycoside" may consist of a single type of alkyl polyglycoside molecules or, as is typically the case, may include a mixture of different alkyl polyglycoside molecules. The different alkyl polyglycoside molecules may be isomeric and/or may be alkyl polyglycoside molecules with differing alkyl groups and/or saccharide portions. By the term "alkyl polyglycoside isomers," reference is meant to alkyl polyglycosides which, although including the same alkyl ether residues, may vary with respect to the location of the alkyl ether residue in the alkyl polyglycoside as well as isomers which differ with respect to the orientation of the functional groups about one or more chiral centers in the molecules. For example, an alkyl polyglycoside can include a mixture of molecules with saccharide portions which are mono-, di- or oligosaccharidesderived from more than one 6 carbon saccharide residue and where the mono-, di- or oligosaccharide has been etherified by reaction with a mixture of fatty alcohols of varying carbon chain length.

Where more than one saccharide residue is present on average per alkyl polyglycoside molecule (i.e., where "n" is greater than 1), the individual saccharide subunits within the same molecule may be identical or different. Where the individual subunits are not all identical, the order and distribution of subunits is typically random. This is not necessarily the case, e.g., where n=2 and the glycoside includes a specific disaccharide, such as sucrose or fructose. It will be understood that the alkyl polyglycoside may include a mixture of different alkyl polyglycoside molecules and/or a mixture of alkyl polyglycoside isomers. Generally, the present alkyl polyglycosides comprise a mixture of alkyl polyglycoside molecules having alkyl groups with varying chain lengths and include a distribution of mono-, di- and oligosaccharides. For example, the alkyl polyglycosides can include a distribution of mono-, di- and oligosaccharides made up of glucosyl residues. The "alkyl group" portion of the alkyl polyglycosides is generally a linear alkyl group (i.e., a straight chain alcohol residue), typically having an even number of carbon atoms. The present alkyl polyglycosides desirably include alkyl groups having 8 to 14 carbon atoms and/or where the average number of carbon atoms in the alkyl chain is 8 to 12 and, desirably, 9 to 11. One example of a suitable alkyl polyglycoside is a mixture of alkyl polyglycoside molecules with alkyl chains having 8 to 10 carbon atoms The alkyl polyglycosides can also be characterized in terms of their hydrophilic/lipophilic balance ("HLB"). This can be calculated based on their chemical structure using techniques well known to those skilled in the art. The HLB of the alkyl polyglycosides used in the present methods typically falls within the range of about 10 to about 15. Desirably, the present alkyl polyglycosides have an HLB of at least about 12 and, more desirably, about 12 to 14.

Alkyl polyglycosides in general are known to have excellent surface tension reduction, wetting and dispersant properties. Alkyl polyglycosides can be produced using conventional methodology. For example, U.S. Pat. Nos. 5,527,892 and 5,770,543, the disclosure of which is herein incorporated by reference, describe alkyl polyglycosides and/or methods for their preparation. Since alkyl polyglycosides are derived from saccharides and fatty alcohols, these compounds are readily biodegradable.

Commercially available examples of suitable alkyl polyglycosides include Glucopon 220, 225, 425, 600 and 625, all available from Henkel Corporation. These products are all mixtures of alkyl mono- and oligoglucopyranosides with alkyl groups based on fatty alcohols derived from coconut and/or palm kernel oil. Glucopon 220, 225 and 425 are examples of particularly suitable alkyl polyglycosides. Glucopon 220 is an alkyl polyglycoside which contains an average of 1.4 glucosyl residues per molecule and a mixture of 8 and 10 carbon alkyl groups (average carbons per alkyl chain-9.1). Glucopon 225 is a related alkyl polyglycoside with linear alkyl groups having 8 or 10 carbon atoms (average alkyl chain-9.1 carbon atoms) in the alkyl chain. Glucopon 425 includes a mixture of alkyl polyglycosides which individually include an alkyl group with 8, 10, 12, 14 or 16 carbon atoms (average alkyl chain-10.3 carbon atoms). Glucopon 600 includes a mixture of alkyl polyglycosides which individually include an alkyl group with 12, 14 or 16 carbon atoms (average alkyl chain 12.8 carbon atoms). Glucopon 625 includes a mixture of alkyl polyglycosides which individually include an alkyl group having 12, 14 or 18 carbon atoms (average alkyl chain 12.8 carbon atoms). Another example of a suitable commercially available alkyl polyglycoside is TL 2141, a Glucopon 220 analog available from ICI.

Vaginal tampons suitable for use in this invention are usually made of absorbent fibers, including natural and synthetic fibers, compressed into a unitary body of a size which may easily be inserted into the vaginal cavity. They are normally made in an elongated cylindrical form in order that they may have a sufficiently large body of material to provide the required absorbing capacity, but may be made in a variety of shapes. The tampon may or may not be compressed, although compressed types are now generally preferred. The tampon may be made of various fiber blends including both absorbent and nonabsorbent fibers, which may or may not have a suitable cover or wrapper. The cover or wrapper for absorbent products, such as tampons and sanitary napkins, is often made from a sheet of spunbonded fibers, e.g., a spunbond polypropylene sheet.

In one embodiment, the present absorbent product includes a porous cover sheet which typically contains at least about 3 wt. %, desirably no more than about 16 wt. % and, more desirably, about 5 to about 10 wt. % alkyl polyglycoside (as add-on wt. %). A suitable example of such an absorbent product is a catamenial tampon having a porous cover sheet which includes the alkyl polyglycoside. Typically, such a tampon would have a cover sheet formed from spunbond fibers of a hydrophobic polymeric material, e.g., a spunbond polypropylene cover layer, with the alkyl polyglycoside coated on the outside of the fibers. In another embodiment, the absorbent product can be a sanitary napkin which includes an absorbent distribution layer incorporating the alkyl polyglycoside. Sanitary napkins of this type would typically have an absorbent distribution layer which includes at least about 5 wt. % of the alkyl polyglycoside and desirably no more than about 15 wt. % of the alkyl polyglycoside (as add-on wt. %).

The fibers from which the present absorbent products are made may be produced, for example, by the meltblowing or spunbonding processes, including those producing bicomponent, biconstituent or polymer blend fibers which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving foraminous mat or belt to form the nonwoven fabric. The fibers produced in the spunbond and meltblown processes are microfibers as defined above. The manufacture of spunbond and meltblown webs is discussed generally above.

As mentioned, the nonwoven also may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable bonding method, particularly when using bicomponent staple fibers, is through-air bonding.

The present absorbent articles contain an effective amount of the inhibiting alkyl polyglycoside compound to substantially inhibit the formation of exoproteins such as TSST-1 when the absorbent product, such as a tampon or sanitary napkin, is exposed to Gram positive bacteria. Where the alkyl polyglycoside is present as part of an absorbent layer of an absorbent product, at least about 0.005 millimoles of alkyl polyglycoside compound per gram of an absorbent may be effective for reducing exoprotein production. Desirably, the product includes at least about 0.05 millimoles alkyl polyglycoside compound per gram of absorbent and, more desirably, about 0.1 millimoles per gram of absorbent to about 2.0 millimoles per gram of absorbent. Although "compound" is used in the singular, one skilled in the art would understand that it includes the plural. That is, the absorbent article can include more than one type of alkyl polyglycoside molecule.

Where the alkyl polyglycoside is formulated as a composition which includes a pharmaceutically acceptable carrier, the composition typically contains at least about 0.01% (wt/vol) and desirably at least about 0.04% (wt/vol) alkyl polyglycoside (based on the total weight of the formulation). Generally, the composition contains no more than about 0.3% (wt/vol) alkyl polyglycoside. Particularly suitable formulations for use in vaginal cleansing applications can contain at least about 0.25 mmol, desirably no more than about 5 mmol and, more desirably about 0.5 to 3 mmol of the alkyl polyglycoside. Formulations which include about 1 to 2 mmol of the alkyl polyglycoside are typically employed in the present methods.

It is generally not necessary to impregnate the entire absorbent body of an absorbent product, such as a tampon, with the inhibitory agent. Optimum results both economically and functionally, can often be obtained by concentrating the material on or near an outer surface where it will be most effective during use.

An exemplary absorbent material is a nonwoven web composed of 3.0 denier polyethylene 5 sheath/polypropylene core bicomponent staple fibers having a length of 38 millimeters. Such bicomponent fibers can be obtained from Chisso Corporation and are typically supplied with a vendor fiber finish. The staple fibers can be sent through an opener and uniformly mixed together before being carded into a web at a line speed of 15.24 meters per minute (50 feet per minute). Once the web is formed, it can be sent through a through-air bonder (drum type) with an air temperature of 131° C. Typical dwell times within the bonder are between 3 and 4.5 seconds. The resultant web, which has a basis weight of 100 gsm and a density of 0.06 gm/cm$^3$, can then be wound up on a roll.

Other suitable absorbent materials include materials which include hydrophilic natural and/or synthetic fibers. For example, a material formed from a mixture of cotton and rayon fibers is an absorbent material that can be used to form the absorbent core of absorbent products such as tampons and sanitary napkins.

The alkyl polyglycoside treating composition may contain other additives as appropriate for the desired result so long as they do not have a major detrimental effect on the activity of the alkyl polyglycoside. Examples of such additives include additional conventional surfactants, such as esters like cetiol (myreth-3-myristate), ethoxylated hydrocarbons or ionic surfactants, or co-wetting aids such as low molecular weight alcohols. As mentioned, the composition is desirably applied from high solids, advantageously 80% or less solvent or water, so as to minimize drying and its attendant costs and deleterious effects. The treating composition may be applied in varying amounts depending on the desired results and application. For sanitary napkin distribution layer applications, for example, effective results can be obtained within a range of about 5% to about 20 wt. % solids (add-on) based on the dry weight of the fabric, with a range of about 6 wt. % to 10 wt. % being advantageous from the perspective of both cost and performance. As used herein, the term "add-on wt. %" refers to the amount of alkyl polyglycoside employed as a percentage of the dry weight of the uncoated substrate. Thus, 10 wt. % (add-on) is equal to 9.1 wt. % based on the total weight of the coated substrate (10/110=9.1). Unless otherwise explicitly stated herein, all amounts of alkyl polyglycoside on a substrate (absorbent or non-absorbent) are stated in terms of add-on wt. %, even though often simply referred to as "wt. %". This is not the case for amounts of alkyl polyglycoside present as part of a fluid composition, where the amounts are stated either in mmolar or % (w/v) as a percentage of the total composition. The actual amount can be readily selected by those skilled in the art based on the teaching of this application. For example, a catamenial tampon designed to be inserted into a body cavity and subsequently in intimate contact with the vaginal epithelium may require substantially less alkyl polyglycoside than an absorbent article worn exterior to the body.

As will be recognized by those skilled in this art, many substrate materials may be employed in the present method including nonwovens such as spunbond, meltblown, carded webs and others as well as woven webs and even films and the like where improved fluid distribution is desired. It will also be recognized by those skilled in this art that some alkyl polyglycoside may be used as internal additives, that is, added to the polymer melt directly or in a concentrate form. After fiber formation, such additives can migrate to the fiber surface and impart the desired effect. For further discussion of internal addition of additives, see for example, U.S. Pat. No. 5,540,979, the contents of which are incorporated herein by reference. The substrate basis weight is not critical and may vary widely depending on the application. For sanitary napkin distribution layer applications, spunbond and bonded carded webs are often used with basis weights generally in the range of from about 7 gsm to about 175 gsm.

The compositions may be applied to the absorbent article using conventional methods for applying an inhibitory agent to the desired absorbent article. For example, unitary tampons without separate wrappers, may be dipped directly into a liquid bath having the agent and then can be air dried, if necessary to remove any volatile solvents. For compressed tampons, impregnating of any of its elements is best done before compressing. The compositions when incorporated on and/or into the tampon materials may be fugitive, loosely adhered, bound, or any combination thereof. As used herein the term "fugitive" means that the composition is capable of migrating through the tampon materials. For example, the alkyl polyglycoside may be blended together with a polymeric material that is to be processed into a component of an absorbent or non-absorbent product.

Alternatively, an alkyl polyglycoside containing solution may be applied directly onto an individual layer of material before it is incorporated into an article to be manufactured, such as an absorbent product. For example, an aqueous solution containing the alkyl polyglycoside can be sprayed onto the surface of a porous cover sheet or absorbent layer designed to be incorporated into an absorbent product. This can be done either during the production of the individual layer or during a fabrication process which incorporates the layer into the article being manufactured.

Nonwoven webs coated with alkyl polyglycoside can be prepared by conventional processes. For example, alkyl polyglycoside can be applied to one or both sides of a traveling web. It will be appreciated by those skilled in the art that the application can be carried out as an inline treatment or as a separate, offline treatment step. A web, such as a spunbond or meltblown nonwoven, can be directed over support rolls to a treating station including rotary spray heads for application to one side of web. An optional treating station may include rotary spray heads to apply the alkyl polyglycoside to the opposite side of the web. Each treatment station generally receives a supply of treating liquid from a reservoir. The treated web may then be dried if needed by passing over dryer cans or other drying means and then wound as a roll or converted to the use for which it is intended. Alternative drying apparatus such as ovens, through air dryers, infra red dryers, air blowers, and the like may also be utilized.

One example of a representative personal care product is a catamenial tampon which includes alkyl polyglycoside. The alkyl polyglycoside may be incorporated into the absorbent portion of the tampon and/or on or in a cover layer. Tampons with an alkyl polyglycoside, such as Glucopon 220, deposited on the cover layer are particularly suitable for inhibiting the production of bacterial exoproteins by Gram positive bacteria such as S. aureus.

The compositions of the present invention can be prepared and applied in other suitable forms, including without limitation, aqueous solutions, lotions, balms, gels, salves, ointments, boluses, suppositories, and the like. For example, the active component of the compositions of this invention can be formulated into a variety of formulations such as those employed in current commercial douche formulations, or in higher viscosity douches. The compositions of this invention may also contain preservatives. Compounds which can impart greater viscosity, such as propylene glycol, may also be added to the compositions of this invention. Generally, higher viscosity compositions are preferred in order to create formulations that will tend to remain in the vagina for a relatively long time period after administration.

The inhibitory alkyl polyglycoside composition may additionally employ one or more conventional pharmaceutically-acceptable and compatible carrier materials useful for the desired application. The carrier can be capable of co-dissolving or suspending the materials used in the composition. Carrier materials suitable for use in the instant composition, therefore, include those well-known for use in the cosmetic and medical arts as a basis for ointments, lotions, creams, salves, aerosols, suppositories, gels and the like. A suitable carrier can be comprised of alcohols and surfactants.

The following examples are presented to illustrate the present invention and to assist one of ordinary skill in making and using the same. The examples are not intended in any way to otherwise limit the scope of the invention.

EXAMPLES

Example A

The effect of Glucopon 220 on growth of S. aureus and production of TSST-1 was examined by placing the desired concentration, expressed in millimoles/milliliter (millimolar hereinafter mM), in 100 mL of a growth medium in a sterile, 500 mL Corning fleaker™.

The growth medium was prepared as follows: 37 grams of brain heart infusion broth (BHI) was dissolved in 880 mL distilled water and sterilized. BHI broth is available from Difco™ Laboratories, Becton Dickinson Microbiology Systems, Cockeysville, Md. 21030-0243. The BHI was supplemented with 100 mL fetal bovine serum (FBS) available from Sigma Chemical Company, P.O. Box 14508, St Louis, Mo. 63178-9916. Ten mL of a 0.021 molar sterile solution of the hexahydrate of magnesium chloride (Sigma Chemical Company) was added to the BHI-FBS mixture. Ten mL of a 0.027 molar sterile solution of L-glutamine (Sigma Chemical Company) was also added to the BHI-FBS mixture.

Glucopon 220 was added directly to the growth medium, sterilized, and diluted in sterile growth medium to obtain the desired final concentrations.

In preparation for inoculation of the fleakers of growth medium containing Glucopon 220, an inoculating broth was prepared as follows: S. aureus MN8 was streaked onto a tryptic soy agar plate (TSA; Difco Laboratories) and incubated at 35° C. The test organism in this example was obtained from Dr. Pat Schlievert, Department of Microbiology, University of Minnesota Medical School, Minneapolis, Min. After 24 hours of incubation three to five individual colonies were picked with a sterile inoculating loop and used to inoculate the 10 mL of growth medium. The tube of inoculated growth medium was incubated at 35° C. in atmospheric air. After 24 hours of incubation, the culture was removed from the incubator and mixed well on a S/P brand vortex mixer. A second tube containing 10 mL of the growth medium was inoculated with 0.5 mL of the above 24 hour old culture and incubated at 35° C. in atmospheric air. After 24 hours of incubation the culture was removed from the incubator and mixed well on a S/P brand vortex mixer. The optical density of the culture fluid was determined in a microplate reader (Bio-Tek Instruments, Model EL309, Box 998, Winooski, Vermont 05404-0998). The amount of inoculum necessary to give $5 \times 10^6$ CFU/mL was determined using a previously prepared standard curve.

The experiment included fleakers of growth medium without Glucopon 220 (control) or with varying concentrations of Glucopon 220. Each fleaker was inoculated with the amount of inoculum determined as described above. The fleakers were capped with sterile aluminum foil and incubated at 35° C. in atmospheric air in a Lab-Line orbital water bath at 180 rpm. The Lab-Line bath was obtained from VWR Scientific Products, 1430 Waukegan Road, McGaw Park, Ill. 60085. Five milliliter samples were removed at the desired time points and the optical density of the culture fluid was determined. The culture fluid was assayed for the number of colony forming units of S. aureus using standard plate count procedures.

After 24 hours of incubation, the experiment was repeated using fresh medium. However, in this instance, the inoculum was from the 24-hour old fleaker containing the same concentration of Glucopon 220. The method described above for determining the amount of fluid necessary to obtain a $5 \times 10^6$ CFU/mL inoculum was used. For example, S. aureus grown in 2 mM Glucopon 220 were inoculated into fresh growth medium containing 2 mM Glucopon 220. Glucopon 220 was tested at 20, 10, 4, 2, 1, and 0.5 mM concentrations. No growth was observed in the presence of the 10 and 20 mM concentrations. Growth was not observed in the growth medium containing 4 mM Glucopon 220 until 26 hours after inoculation, thus it was not reinoculated into fresh medium after the first 24 hours of incubation.

Five milliliters of the remaining culture fluid was prepared for the analysis of TSST-1 as follows: the culture fluid was centrifuged at 2500 rpm at 2–10° C. for 15 minutes. The supernatant was filter sterilized through an Autovial® 5 syringeless filter, 0.2 uM pore size (Whatman, Inc., Clifton, N.J.). The resulting fluid was frozen at −70° C. in a Fisherbrand® 12×75 mm polystyrene culture tube, Fisher Scientific, 585 Alpha Drive, Pittsburgh, Pa. 15328.

The amount of TSST-1 per mL was determined by a non-competitive, sandwich enzyme-linked immunoabsorbent assay (ELISA). Samples of the culture fluid and the TSST-1 reference standard were assayed in triplicate. The method employed was as follows: four reagents, rabbit polyclonal anti-TSST-1 IgG (LTI-101), rabbit polyclonal anti-TSST-1 IgG conjugated to horseradish peroxidase (#LTC-101), TSST-1 (#TT-606), and normal rabbit serum (NRS) certified anti-TSST-1 free (#NRS-10) were purchased from Toxin Technology, Inc., 7165 Curtiss Avenue, Sarasota, Fla. 34231. A 10 ug/mL solution of the polyclonal rabbit anti-TSST-1 IgG was prepared in phosphate buffered saline (PBS), pH 7.4. The PBS was prepared from 0.016 molar $NaH_2PO_4$, 0.004 molar $NaH_2PO_4\text{-}H_2O$, 0.003 molar KCl and 0.137 molar NaCl, all available from Sigma Chemical Company. One hundred microliters of the polyclonal rabbit anti-TSST-1 IgG solution was pipetted into the inner wells of polystyrene microplates, catalogue #439454, obtained from Nunc-Denmark. The plates were covered and incubated at room temperature overnight. Unbound anti-toxin was removed by draining until dry.

TSST-1 was diluted to 10 ng/mL in PBS with phosphate buffered saline (pH 7.4) containing 0.05% (vol/vol) Tween-20 (PBS-Tween) available from Sigma Chemical Company and 1% NRS (vol/vol) and incubated at 4° C. overnight. Test samples were combined with 1% NRS (vol/vol) and incubated at 4° C. overnight.

One hundred microliters of a 1% (wt/vol) solution of the sodium salt of casein in PBS (Sigma Chemical Company) was pipetted into the inner wells of polystyrene microplates, the plates were covered, and incubated at 35° C. for one hour. Unbound BSA was removed by 3 washes with PBS-Tween. TSST-1 reference standard (10 ng/mL) treated with NRS, test samples treated with NRS, and reagent controls were pipetted in 200 microliter volumes to their respective wells on the first and seventh columns of the plate. One hundred microliters of PBS-Tween was added to the remaining wells. The TSST-1 reference standard and test samples were then serially diluted 5 times in the PBS-Tween by transferring 100 microliters from well-to-well. The samples were mixed prior to transfer by repeated aspiration and expression. This was followed by incubation for 1.5 hours at 35° C. and five washes with PBS-T and three washes with distilled water to remove unbound toxin.

The rabbit polyclonal anti-TSST-1 IgG conjugated to horseradish peroxidase was diluted according to manufacturer's instructions and 50 microliters was added to each microtiter well, except well A-1, the conjugate control well. The plates were covered and incubated at 35° C. for one hour.

Following incubation, the plates were washed five times in PBS-Tween and three times with distilled water. Following the washes, the wells were treated with 100 microliters of a horseradish peroxidase substrate buffer consisting of 5 mg of o-phenylenediamine and 5 microliters of 30% hydrogen peroxide (both from Sigma Chemical Company) in 11 mL of citrate buffer, pH 5.5. The citrate buffer was prepared from 0.012 anhydrous citric acid and 0.026 molar dibasic sodium phosphate both available from Sigma Chemical Company. The plates were incubated for 15 minutes at 35° C. The reaction was stopped by the addition of 50 microliters of a 5% sulfuric acid solution. The intensity of the color reaction in each well was evaluated using the BioTek Model EL309 microplate reader (OD 490 nm). TSST-1 concentrations in test samples were determined from the reference toxin regression equation derived during each assay procedure.

The efficacy of Glucopon 220 in inhibiting the production of TSST-1 is shown in Table I below. The data is presented in units of TSST-1 (ng/OD units) as well as showing the TSST-1 levels as a percentage of the untreated control.

TABLE I

| Glucopon 220 (mM) | OD (10 hr) | TSST-1 (ng/OD units) | TSST-1 (% of control) | OD (24 hr) | TSST-1 (ng/OD units) | TSST-1 (% of control) |
|---|---|---|---|---|---|---|
| | | First 24 hour incubation | | | | |
| None | 7.49 | 189 | | 11.47 | 1471 | |
| 4 mM | 0.03 | ND | — | 0.04 | ND | — |
| 2 mM | 7.95 | 23 | 12% | 11.47 | 37 | 3% |
| 1 mM | 8.1 | 63 | 33% | 11.21 | 168 | 11% |
| 0.5 mM | 7.45 | 143 | 76% | 10.71 | 187 | 13% |
| | | Second 24 hour incubation in fresh medium | | | | |
| None | 6.34 | 232 | — | 10.00 | 1141 | — |
| 2 mM | 7.91 | 12 | 8% | 11.93 | 37 | 3% |
| 1 mM | 6.89 | 41 | 17% | 9.92 | 127 | 11% |

Example B

Tampon prototypes with cover sheets treated with a variety of different non-ionic surface treatments were examined in a laboratory microbial challenge test to determine the effect of surface treatments on TSST-1 production by *Staphylococcus aureus*.

Cover sheet material was produced by coating the particular non-ionic surface treatment onto a commercially produced 0.4 osy polypropylene spunbond cover material. The surface treatment was applied by diluting the surfactant to the desired concentration with purified water and applying the solution to the nonwoven cover sheet material with a Butterworth treater. The amount of solution applied was controlled by nip pressure and line speed.

The coated cover sheet was used to fabricate tampon prototypes containing an absorbent layer made up of a mixture of cotton and rayon fibers. An uncompressed absorbent pledget made of the combination of cotton and rayon fibers was covered with the treated spunbond cover material. A string hole was punched through the uncompressed pledget. A string was knotted and looped through the absorbent pledget and cover and the resulting construction was compressed and placed in a tampon applicator.

The add-on level of the various cover sheet surface treatments was determined by the weight of extractables. Correction was made for the level of extractables obtained from untreated cover material, extraction efficiency for the particular surfactant and the solids content of the surfactants. The treated spunbond cover sheets were sampled in triplicate and the recovery efficiency was calculated from triplicate testing of one add-on level for each surfactant. As controls, spiked samples were prepared using untreated nonwoven cover sheet material and reference samples of the various surfactants. The spiked samples were subjected to the same extraction conditions as the corresponding coated cover sheet materials.

Tampon prototypes to be tested were randomly selected from each of the groups of protoypes with varying types of cover sheet coating. The prototypes were grasped with sterile forceps. The string was cut off with sterile scissors, and the pledget placed into a sterile, capped polystyrene test tube with the string end down.

Each pledget was inoculated with 10.5 mL of an inoculating broth containing $5\times10^6$ CFU/mL of *S. aureus* MN8

(obtained from Dr. Pat Schlievert, Department of Microbiology, University of Minnesota Medical School, Minneapolis, Minn.). After incubation at 35° C. for 24 hours in plugged tubes, the pledgets were placed into sterile stomacher bags and sterile fluid was added. The pledgets and fluid were then stomached. Using sterile technique, aliquots of fluid were removed from the stomacher bag and placed into sterile tubes for testing.

Assay for TSST-1 Concentration

Five milliliters of the culture fluid was prepared for the analysis of TSST-1 as follows: the culture fluid was centrifuged at 9000 rpm at 4° C. for 5 minutes. The supernatant was filter sterilized through 0.45 micron filter and frozen at −70° C. in two aliquots in 1.5 mL polypropylene screw cap freezer vials.

The amount of TSST-1 per mL was determined by a non-competitive, sandwich enzyme-linked immunoabsorbent assay (ELISA). Samples of the culture fluid and the TSST-1 reference standard were assayed in triplicate. The method employed was as follows: four reagents, rabbit polyclonal anti-TSST-1 IgG (LTI-101), rabbit polyclonal anti-TSST-1 IgG conjugated to horseradish peroxidase (#LTC-101), TSST-1 (#TT-606), and normal rabbit serum (NRS) certified anti-TSST-1 free (#NRS-10) were purchased from Toxin Technology, Inc., 7165 Curtiss Avenue, Sarasota, Fla. 34231. Sixty-two microliters of polyclonal rabbit anti-TSST-1 IgG (#LTI-101) was appropriately diluted so that a 1:100 dilution gave an absorbance of 0.4 at 205 nanometers. This was added to 6.5 mL of 0.5 molar carbonate buffer, pH 9.6, and 100 ul of the solution was pipetted into the inner wells of polystyrene microplates, catalogue #439454, obtained from Nunc-Denmark. The plates were covered and incubated at 37° C. overnight. Unbound anti-toxin was removed by four washes with phosphate buffered saline (pH 7.2) (0.016 molar $NaH_2PO_4$ and 0.9% (w/v) NaCl both available from Sigma Chemical Company) containing 0.5% [vol/vol] Tween 20 (PBS-Tween), also available from Sigma Chemical Company in an automatic plate washer. The plates were treated with 100 ul of a 1% [wt/vol] solution of bovine serum albumin (BSA), fraction V, in the 0.5 molar carbonate buffer described above. BSA fraction V is available from Sigma Chemical Company. The plates were covered and incubated at 37° C. for one hour. Unbound BSA was removed by six washes with 250 ul PBS-Tween. Test samples were treated with normal rabbit serum (10% [vol/vol] final concentration) for 15 minutes at room temperature. TSST-1 reference standard, serially diluted from 1–20 ng/mL in PBS-Tween and the NRS treated test samples (serially diluted in PBS-Tween so that the resultant TSST-1 concentration is between 1–20 ng), were pipetted in 100 ul volumes to their respective wells. This was followed by incubation for two hours at 37° C. and four washes of 250 mL PBS-Tween to remove unbound toxin. The rabbit polyclonal anti-TSST-1 IgG conjugated to horseradish peroxidase was diluted according to manufacturer's instructions. The final use dilution of the conjugate was determined by running standard curves of TSST-1 reference standard with the conjugate at undiluted, 1:2 and 1:4 dilutions. The dilution that gave results most comparable to previous lots of conjugate was selected. One hundred microliter volumes of this dilution was added to each microtiter well. The plates were covered and incubated at 37° C. for one hour.

Following incubation the plates were washed six times in 250 ul PBS-Tween and three times with distilled water. Following the washes, the wells were treated with 100 ul of a horseradish peroxidase substrate solution consisting of 0.015 molar sodium citrate (pH 4.0), 0.6 millimolar 2,2′-Azino-bis-(3-ethylbenzthiazoline-6-sulfonic acid) diammonium salt and 0.009% (vol/vol) hydrogen peroxide, all available from Sigma Chemical Company. The intensity of the color reaction in each well was evaluated over time using a BioTek Model EL340 Microplate reader (OD 405 nm) and Kineticalc® software available from Biotek Instruments, Inc. TSST-1 concentrations in test samples were derived from the reference toxin regression equations for each assay procedure.

The efficacy of Glucopon 220 in inhibiting the production of TSST-1 is shown in Table II below.

TABLE II

| Surface Treatment | Amount (Wt. % Solids) | TSST-1 (ng/mL) | Final [S. aureus] ($\times 10^9$ CFU/ml) |
| --- | --- | --- | --- |
| Laureth-4 | 7 wt. % | 531.8 | 4.57 |
| PPG-5 Laureth-5 | 18 wt. % | 609.2 | 3.82 |
| Glucopon 220 | 3 wt. % | 554.8 | 6.41 |
| Glucopon 220 | 14 wt. % | 327.5 | 6.99 |
| Steareth-2 | 8 wt. % | 680.7 | 5.76 |

Example C

The effect of Glucopon 220 on growth of S. aureus and production of alpha-toxin (alpha-hemolysin) was determined by placing the desired concentration, expressed in millimoles/milliliter (millimolar hereinafter mM), in 100 mL of a growth medium in a sterile, 500 mL Corning fleaker™. Glucopon 220 was added directly to the growth medium, filter sterilized, and diluted in sterile growth medium to obtain the desired final concentrations.

The experiment was conducted following the procedure described in Example A except that the test organism in this example, S. aureus RN6390, was obtained from Dr. Richard Novick, The Skirball Institute for Biomolecular Medicine, New York University Medical Center, New York, N.Y. The experiment included fleakers of growth medium without Glucopon 220 (control) or with varying concentrations of Glucopon 220. Each fleaker was inoculated with S. aureus RN6390 following the procedure described in Example A. The fleakers were capped with sterile aluminum foil and incubated at 35° C. for 24 hours in atmospheric air in a Lab-Line orbital water bath at 180 rpm.

Five milliliters of the culture fluid was prepared for the analysis of alpha-hemolysin as follows: the culture fluid was adjusted to a standard absorbance (1.0) and centrifuged at 2500 rpm at 2–10° C. for 15 minutes. The supernatant was filter sterilized through an Autovial® 5 syringeless filter, 0.2 micron pore size (Whatman, Inc., Clifton, N.J.). The resulting fluid was frozen at −20° C. in a Fisherbrand® 12×75 mm polystyrene culture tube, Fisher Scientific, 585 Alpha Drive, Pittsburgh, Pa. 15328.

The amount of alpha-hemolysin was determined by a hemolytic assay using rabbit red blood cells. The method employed was as follows: defibrinated rabbit red blood cells (rrbc; Remel) were washed 3 times in a Tris-saline buffer consisting of 50 mM Tris/Tris-HCl and 100 mM NaCl, pH 7.0. Centrifugation was at 800×g for 7 minutes. The reagents were obtained from Sigma Chemical Corporation. The rrbc were suspended in 200 mL Tris-saline buffer to a concentration of 0.5%. The culture supernatants were serially diluted in the culture medium. One part diluted sample was combined with 9 parts rrbc. All sample assays were run in triplicate. Controls for hemolysis consisted of a negative control (one part Tris-saline buffer to 9 parts rrbc) and a positive control (one part 10% SDS to 9 parts rrbc). Ten replicas of the controls were prepared. All assay samples were incubated at 37° C. for 30 minutes, then centrifuged at 800×g for 10 minutes. The amount of hemolysis in the samples and controls was measured at 405 nm in a BioTek Model EL309 microplate reader. Units of activity are expressed as the reciprocal of the dilution of each test sample giving 50% lysis.

The effect of Glucopon 220 on alpha-toxin production is shown in Table III below.

TABLE III

| Glucopon 220 (mM) | Alpha-hemolysin units | Alpha hemolysin (% of control) |
|---|---|---|
| None | 32 | |
| 2 mM | 0 | 0.0% |
| 1 mM | 2.2 | 6.9% |
| 0.5 mM | 4.4 | 13.8% |

Throughout this application various publications are referenced. The disclosures of these publications in their entireties are hereby incorporated by reference into this application in order to more fully describe the state of the art to which this invention pertains.

The invention has been described with reference to various specific and illustrative embodiments and techniques. However, it should be understood that many variations and modifications may be made while remaining within the spirit and scope of the invention.

What is claimed is:

1. A method of inhibiting the production of exoprotein from Gram positive bacteria located in and around the vagina, the method comprising exposing the Gram positive bacteria to a liquid vaginal cleansing composition comprising a pharmaceutically acceptable carrier and an effective amount of an alkyl polyglycoside, having the general formula $$H-(Z)_n-O-R$$

wherein Z is a saccharide residue having 5 or 6 carbon atoms, n is 4–6, and R is an alkyl group having 8 to 18 carbon atoms, and wherein the alkyl polyglycoside has a hydrophilic/lipophilic balance of at least 10.

2. The method of claim 1, wherein the alkyl polyglycoside is present in the composition in an amount of at least about 0.01% (wt/vol).

3. The method of claim 1, wherein the alkyl polyglycoside is present in the composition in an amount of at least about 0.04% (wt/vol).

4. The method of claim 1, wherein the alkyl polyglycoside is present in the composition in an amount of no more than about 0.3% (wt/vol).

5. The method of claim 1, wherein the alkyl polyglycoside has an alkyl group having from 8 to 14 carbon atoms.

6. The method of claim 1, wherein the alkyl polyglycoside has an alkyl group having from 8 to 10 carbon atoms.

7. The method of claim 1, wherein the alkyl polyglycoside has a hydrophilic/lipophilic balance of 10 to 15.

8. The method of claim 1, wherein the alkyl polyglycoside has a hydrophilic/lipophilic balance of 12 to 14.

9. The method of claim 1, wherein the composition additionally comprises an additive selected from the group consisting of myreth-3-myristate, glycerol monolaurate, laureth-4, ascorbic acid, sodium bisulfite, and vitamin E.

10. The method of claim 1, wherein the composition is used in combination with a product selected from the group consisting of sanitary napkins, panty liners, adult incontinent undergarments, diapers, medical bandages, incontinence devices, barrier birth control devices, and contraceptive sponges.

11. A method of inhibiting the production of exoprotein from Gram positive bacteria located in and around the vagina, the method comprises exposing the Gram positive bacteria to a liquid vaginal cleansing composition comprising a pharmaceutically acceptable carrier and an effective amount of an alkyl polyglycoside, wherein the alkyl polyglycoside is selected from the group consisting of Glucopon 220, Glucopon 225, Glucopon 425, Glucopon 600, and Glucopon 925.

* * * * *

UNITED STATES PATENT AND TRADEMARK OFFICE
CERTIFICATE OF CORRECTION

PATENT NO. : 6,656,913 B1
DATED : December 2, 2003
INVENTOR(S) : Resheski-Wedepohl et al.

It is certified that error appears in the above-identified patent and that said Letters Patent is hereby corrected as shown below:

Column 1,
Line 63, "and, excrete" should read -- and excrete --.

Column 2,
Lind 28, "such" should read -- such as --.

Column 3,
Line 1, "toxins. A," should read -- toxins A, --.
Line 33, "described" should read -- described in --.

Column 5,
Line 13, "etc. and" should read -- etc., and --.
Line 15, ""polymer" should read -- "polymer" --

Column 6,
Line 60, "oligosaccahridesderived" should read -- oligosaccharides derived --.

Column 11,
Line 4, "web" should read -- the web --.
Line 66, "St Louis" should read -- St. Louis --.

Column 18,
Line 34, "comprises" should read -- comprising --.
Line 40, "925." should read -- 625. --.

Signed and Sealed this

Eleventh Day of May, 2004

JON W. DUDAS
*Acting Director of the United States Patent and Trademark Office*